United States Patent [19]

Peng et al.

[11] Patent Number: 5,753,716
[45] Date of Patent: May 19, 1998

[54] USE OF ALUMINUM PHOSPHATE AS THE DEHYDRATION CATALYST IN SINGLE STEP DIMETHYL ETHER PROCESS

[75] Inventors: Xiang-Dong Peng, Allentown; Gene E. Parris, Coopersburg; Bernard A. Toseland; Paula J. Battavio, both of Allentown, all of Pa.

[73] Assignee: Air Products and Chemicals, Inc., Allentown, Pa.

[21] Appl. No.: 803,608

[22] Filed: Feb. 21, 1997

[51] Int. Cl.$^6$ ............................................. C07C 27/00
[52] U.S. Cl. ............................................. 518/700; 502/208
[58] Field of Search ............................. 518/700, 713, 518/714; 502/208

[56] References Cited

U.S. PATENT DOCUMENTS

| Re. 34,911 | 4/1995 | Glemza | 423/305 |
|---|---|---|---|
| 3,342,750 | 9/1967 | Kearby | 252/437 |
| 3,879,310 | 4/1975 | Rigge et al. | 252/435 |
| 3,904,550 | 9/1975 | Pine | 252/437 |
| 3,969,273 | 7/1976 | Brown et al. | 252/435 |
| 4,066,572 | 1/1978 | Choca | 252/437 |
| 4,080,311 | 3/1978 | Kehl | 252/437 |
| 4,098,809 | 7/1978 | Pagani | 260/449 R |
| 4,177,167 | 12/1979 | Manara et al. | 252/455 R |
| 4,233,184 | 11/1980 | Cull | 252/437 |
| 4,341,069 | 7/1982 | Bell et al. | 60/39.02 |
| 4,375,424 | 3/1983 | Slaugh | 252/463 |
| 4,417,000 | 11/1983 | Slaugh et al. | 518/713 |
| 4,423,155 | 12/1983 | Bell et al. | 502/38 |
| 4,536,485 | 8/1985 | Topp-Jorgensen | 502/62 |
| 4,595,785 | 6/1986 | Brake | 568/698 |
| 4,605,788 | 8/1986 | Brake | 568/698 |
| 4,845,069 | 7/1989 | Fellmann | 502/208 |
| 5,030,431 | 7/1991 | Glemza | 423/305 |
| 5,218,003 | 6/1993 | Lewnard et al. | 518/700 |
| 5,292,701 | 3/1994 | Glemza et al. | 502/202 |
| 5,389,689 | 2/1995 | Fujimoto et al. | 518/700 |
| 5,552,361 | 9/1996 | Reiser | 508/208 |

FOREIGN PATENT DOCUMENTS

| 1085824 | 4/1994 | China . |
|---|---|---|
| 1087033 | 5/1994 | China . |
| 1090222 | 8/1994 | China . |
| 0215336 | 3/1987 | European Pat. Off. . |
| 0169953 | 10/1987 | European Pat. Off. . |
| 0324475 | 1/1993 | European Pat. Off. . |
| 0591538 | 4/1994 | European Pat. Off. . |
| 291937 | 7/1991 | Germany . |
| 2280836 | 4/1989 | Japan . |
| 285224 | 3/1990 | Japan . |
| 38446 | 1/1991 | Japan . |
| 3181435 | 4/1993 | Japan . |
| 2097382 | 11/1984 | United Kingdom . |

OTHER PUBLICATIONS

Journal Chem Soc. Faraday Trans. "Effect of Phosphate Iones on the Surface Chemistry and Microstructure of Amorphous Alumnia", Abbattista, 86 (21)3653–3658, 1990.
J. of Cat. "Influence of the Starting Aluminum Salt on the Surface Acid Properties of AlPO4 Catalysts Precipitated with Ammonium Hydroxide", Campelo, 111, 106–119, 1988.
J. of Cat. "Conversion of Alcohols (alpha methylated series) on AlPO4 Catalysts", Campelo, 151, 307–314, 1995.
Sofianos and Scurrell, Conversion of Synthesis Gas to Dimethyl Ether over Bifunctional Catalytic Systems, Ind. Eng. Chem. Res, 1991, 30, 2372–2378.
Cai et al, Light Alkenes from Syngas via Dimethyl Ether, Applied Catalysis A: General 125 (1995) 29–38.
Peng, et al, Catalyst Activity Maintenance Study for the Liquid Phase Dimethyl Ether Process, Proceedings of Coal Liquefaction and Gas Conversion Contractors Review Conference, Pittsburgh, 1995, p. 371.
A. Stiles, Catalyst Manufacture —Laboratory and Commercial Preparations, Marcel Dikker, Inc., New York, 1983.

*Primary Examiner*—C. Warren Ivy
*Assistant Examiner*—Jean F. Vollano
*Attorney, Agent, or Firm*—Robert J. Wolff

[57] ABSTRACT

The present invention pertains to a process for the coproduction of methanol and dimethyl ether (DME) directly from a synthesis gas in a single step (hereafter, the "single step DME process"). In this process, the synthesis gas comprising hydrogen and carbon oxides is contacted with a dual catalyst system comprising a physical mixture of a methanol synthesis catalyst and a methanol dehydration catalyst. The present invention is an improvement to this process for providing an active and stable catalyst system. The improvement comprises the use of an aluminum phosphate based catalyst as the methanol dehydration catalyst. Due to its moderate acidity, such a catalyst avoids the coke formation and catalyst interaction problems associated with the conventional dual catalyst systems taught for the single step DME process.

4 Claims, 2 Drawing Sheets

USE OF ALUMINUM PHOSPHATE AS THE DEHYDRATION CATALYST IN SINGLE STEP DIMETHYL ETHER PROCESS

STATEMENT REGARDING FEDERALLY SPONSORED RESEARCH OR DEVELOPMENT

This invention was made under DOE Contract DE-FC22-95PC93052 and is subject to government rights arising therefrom.

CROSS-REFERENCE TO RELATED APPLICATIONS

Not applicable.

BACKGROUND OF THE INVENTION

The present invention pertains to the prior art process for the coproduction of methanol and dimethyl ether (DME) directly from a synthesis gas in a single step (hereafter, the "single step DME process"). In this process, the synthesis gas comprising hydrogen and carbon oxides is contacted with a dual catalyst system comprising a physical mixture of a methanol synthesis catalyst and a methanol dehydration catalyst. The objective of the present invention is to provide an active and stable catalyst system for this process.

The advantage of the single step DME process is the high syngas conversion per pass as compared to, for example, the traditional two step process in which methanol is produced from syngas in a reactor over a methanol synthesis catalyst, then converted into DME in a subsequent reactor over a dehydration catalyst.

The catalyst system for the single step DME process possesses two functionalities, namely, a methanol synthesis functionality on which methanol synthesis from syngas is carried out, and a methanol dehydration functionality on which methanol is dehydrated into DME and water. The methanol synthesis catalyst also possesses water gas shift activity. These reactions are shown, respectively, as follows:

$$CO + 2H_2 \rightarrow CH_3OH \qquad (1)$$

$$2CH_3OH \rightarrow CH_3OCH_3 + H_2O \qquad (2)$$

$$CO + H_2O \rightarrow CO_2 + H_2 \qquad (3)$$

There are two types of catalyst systems for the single step DME process. The first type, called the dual catalyst system, consists of a physical mixture of a methanol synthesis catalyst and a methanol dehydration catalyst. The methanol synthesis catalyst is generally a copper and/or zinc and/or aluminum and/or chromium based commercial catalyst while the methanol dehydration catalyst is generally selected from solid acid materials, including γ-alumina, silica alumina, other metal oxides and mixed oxides, crystalline aluminosilicates, crystalline zeolites, clays, phosphates, sulfates, metal halides, acidic resins, supported phosphoric acid, and heteropoly acids. In gas phase applications using a fixed or fluidized bed reactor, the powders of the two catalysts can be mixed followed by being formed into pellets or beads; or, separate pellets or beads can be prepared of the two catalysts. The pellets can be placed in a fixed bed reactor either in well mixed form or in a layer-by-layer arrangement. In liquid phase applications using a slurry bed reactor containing an inert liquid medium, a powder mixture of the two catalysts can be directly used.

In the second type of catalyst system for the single step DME process, the two functionalities are built into a single catalyst. This has been achieved either by coprecipitating methanol synthesis and dehydration components together to form one catalyst, or by precipitating methanol synthesis components onto an existing, high surface area solid acid material.

Regardless of which type of catalyst system is used and regardless of whether the process is conducted in the gas or liquid phase, maintenance of the catalyst activity is a major challenge. This is especially true when a dual catalyst system is used.

An article by A. C. Safianos and M. S. Scurrel entitled "Conversion of Synthesis Gas to Dimethyl Ether over Bifunctional Catalytic Systems" in Ind. Eng. Chem. Res., V30, pp. 2372–2378, 1991 demonstrates rapid deactivation of a bifunctional catalyst system at 275° C. The catalyst was prepared by pressing a powder mixture of a copper-zinc-aluminum methanol synthesis catalyst and γ-alumina into pellets. Oxidative regeneration results in partial recovery of the catalyst activity, followed by even more rapid deactivation.

Constant DME productivity was reported in an article by G. Cai et al. in Applied Catal. A, V125, pp. 29–38, 1995. The reaction was conducted in a fixed bed reactor using a catalyst made of a powder mixture of a methanol synthesis catalyst and modified H-mordenite. However, this apparent constant productivity was maintained by increasing the reactor temperature, from 240° to 320° C. over a period of 2,100 hours.

A recent report by X. D. Peng et al. in an article entitled "Catalyst Activity Maintenance Study for the Liquid Phase Dimethyl Ether Process" in the Proceedings of Coal Liquefaction and Gas Conversion Contractors Review Conference, Pittsburgh, p.371, 1995, shows that, when a powderous physical mixture of a commercial methanol synthesis catalyst and γ-alumina were used in the liquid phase DME process, rapid deactivation occurred to both catalysts.

The catalyst stability problem described above lies on the very concept of the single step DME process. First, it can be due to the great amount of heat released from high syngas conversion, especially in the case of fixed bed operations, because the methanol synthesis reaction is highly exothermic. When a methanol synthesis catalyst is used by itself in a once-through operation in a fixed bed, its activity normally cannot be fully utilized, because the heat released from higher syngas conversion can not be adequately dissipated. This, in addition to the hot spots and temperature over-shooting commonly occurring in fixed bed reactors, would cause the sintering of copper in the methanol catalyst, leading to catalyst deactivation. Since the single step DME process provides much higher syngas conversion per pass, one would expect more severe methanol catalyst deactivation in a fixed bed operation if the potential conversion of the process is to be completely realized.

Secondly, the introduction of the acid functionality into the catalyst system also introduces additional problems. Strong acid sites will cause coke formation, leading to the deactivation of the dehydration catalyst. High temperature in a fixed bed reactor caused by high syngas conversion, hot spots, and temperature over-shooting will make this more of a problem.

The third problem is the compatibility between the methanol synthesis catalyst and the dehydration catalyst, when a dual catalyst system is used. The report by X. D. Peng et al. mentioned above shows that the rapid and simultaneous deactivation of methanol synthesis and dehydration catalysts is caused by a novel mechanism, namely, an interaction between the two catalysts. Again, the problem is related to the acidity of the dehydration catalyst—more rapid deactivation was observed when the dehydration catalyst contains acid sites of greater strength. This detrimental interaction, although not reported in the literature yet, should also occur in the gas phase operation when intimate contact between the two catalysts is provided.

In summary, there are three catalyst stability problems associated with dual catalyst systems used in current single step DME processes: (i) sintering of the methanol catalyst in fixed bed operation; (ii) coke formation on dehydration catalysts; and (iii) detrimental interaction between the methanol synthesis and methanol dehydration catalysts. The first problem is related to heat management, and can be circumvented by employing liquid phase reaction technologies; better heat management can be attained in a slurry phase reaction because of the presence of an inert liquid medium and better mixing. The second and the third problems are related to the acidity of the dehydration catalyst in a dual catalyst system. Therefore, a dehydration catalyst with the right acidity is crucial for the stability of a dual catalyst system.

As documented below, a variety of methanol dehydration catalysts have been taught in the gas phase literature for use in the single step DME processes.

U.S. Pat. No. 4,098,809 to Snamprogetti S.p.A. (1978) teaches a fixed bed syngas-to-DME process. The catalyst system consists of a physical mixture of a copper based or chromium-zinc based methanol synthesis catalyst and a methanol dehydration catalyst such as alumina. An ensuing patent assigned to the same company (U.S. Pat. No. 4,177,167, 1979) teaches an improved dehydration catalyst, i.e., γ-alumina "stabilized" by silicon compounds. The modification was aimed at increasing the stability of the dehydration catalyst by increasing its resistance to heat and mechanical stress as well as the action of steam at high temperatures.

U.S. Pat. No. 4,341,069 to Mobil Oil Corp. (1982) teaches a gas phase process for DME production to be used in conjunction with an integrated gasification combined cycle power plant. Examples in the patent show that the catalyst, consisting of a copper, zinc, chromium or aluminum based methanol catalyst and γ-alumina as the dehydration component, requires frequent regeneration, in some cases on a daily basis.

U.S. Pat. No. 4,417,000 to Shell (1983) describes a gas phase process for the production of DME from syngas over a catalyst comprising a physical mixture of two components. The first component is an alkali metal oxide promoted copper-zinc catalyst supported on an alumina carrier, and the second component is tungsten oxide supported on a carrier selected from silica alumina, silica, or alumina. The catalyst system is described in detail in U.S. Pat. No. 4,375,424.

U.S. Pat. No. 4,423,155 and UK Patent 2,097,382 to Mobil (1983) teach a two-component catalyst for direct conversion of syngas into DME in a single gas phase reactor. The catalyst pellets were made from a powder mixture containing a copper, zinc and chromium or copper, zinc and aluminum coprecipitated methanol synthesis catalyst and an acidic dehydration component selected from γ-alumina, silica alumina, clays, crystalline aluminosilicates, crystalline zeolites, phosphates, titanium oxide in combination with silicon oxide, rare earths, among which only γ-alumina was shown in the examples. The catalyst deactivates rapidly under the reaction conditions (315° C., 100 atm). It can be regenerated to some extent using oxygen for several cycles, but eventually died upon 50 days on stream.

U.S. Pat. No. 4,536,458 to Haldor Topsoe (1985) teaches a methanol dehydration catalyst to be used along with a methanol synthesis catalyst in a gas phase syngas-to-DME process. The catalyst is a base (e.g. NH$_3$ or amines) treated aluminosilicate, selected from zeolite H-ZSM-5, Y-zeolite, and cross-linked natural smectites, followed by re-activation. It is claimed that the treatment reduces the formation of coke, therefore, leading to better stability of the catalyst system.

Japanese Patents 2-280836 (1990) and 3-8446 (1991) to Mitsubishi Heavy Ind. Co., Ltd. describe the methods for preparing syngas-to-DME catalysts. In the first patent, copper, zinc, and aluminum were coprecipitated onto a dehydration catalyst selected from the group of Al$_2$O$_3$, TiO$_2$, Fe$_2$O$_3$, Sn$_2$O$_3$ and ZrO$_2$. The methanol catalyst in the second patent was prepared by coprecipitation of copper, zinc, chromium, and aluminum. The catalyst powder was then mixed with γ-alumina of the same size and pressed into pellets. The catalysts in both patents were tested in a fixed bed reactor and showed good stability over 1000 hours on stream.

German Patent 291 937 to Akad Wissenschaften DDR (1991) describes the use of ZSM-5 along with a methanol catalyst to produce DME from syngas. Both catalyst powders were pelletized together for gas phase applications.

Chinese Patent 1085824 to Dalian Institute of Chemical Physics (1994) teaches a gas phase process and a catalyst for the production of DME from syngas. The catalyst system consists of a commercial methanol synthesis catalyst and γ-alumina modified by oxide of boron, phosphorous, or titanium.

Chinese Patent 1087033 to Dalian Institute of Chemical Physics (1994) teaches a catalyst system featured by a passivated dehydration component. It is either steam treated H-Y zeolite or steam treated H-mordenite. These catalysts are claimed to provide good stability and activity.

Chinese Patent 1090222 to Hubei Chemical Institute (1994) teaches a catalyst system prepared by impregnating γ-alumina beads with the active components normally present in methanol synthesis catalysts, including copper and zinc.

In contrast to the gas phase literature, the work on liquid phase syngas-to-DME processes and catalysts is more limited and recent.

U.S. Pat. No. 5,218,003 and European Patent 324 475 to Air Products and Chemicals Inc. (both 1993) teach a liquid phase DME process. Syngas containing hydrogen, carbon monoxide and carbon dioxide is contacted with a powder mixture of a copper-containing commercial methanol synthesis catalyst and a methanol dehydration catalyst in an inert liquid in a three phase reactor system. The dehydration catalyst is selected from the group of alumina, silica alumina, zeolites, solid acids, solid acid ion exchange resins, and mixtures thereof.

Japanese Patent 3-181435 to NKK Corporation (1991) claims a method of manufacturing DME from syngas in a slurry phase reactor. The conceptual catalyst is a combination of copper-zinc or zinc-chromium based methanol synthesis catalysts, methanol dehydration catalysts selected from the group of γ-alumina, silica, alumina, zeolite, etc., and copper-zinc or iron-chromium based water gas shift catalysts. The catalysts were used in form of powders suspended in a solvent.

U.S. Pat. No. 5,389,689 to the same company (1995) and its equivalent European Patent 591 538 (1994) teach a catalyst system for a slurry phase single step DME process. The catalyst was prepared by pulverizing a powder mixture of a copper based methanol catalyst and a pure or copper oxide doped alumina, compressing to bind said oxides, and then pulverizing again to form powders to be used in a slurry reactor.

In addition to dehydration catalysts used in the dual catalyst system of the single step DME process, the prior art also teaches catalysts which are specifically designed for methanol dehydration to DME and not necessarily for mixing with a methanol synthesis catalyst. U.S. Pat. No. 4,595,785 and 4,605,788 and European Patent 169 953 to DuPont teach improved methanol dehydration catalysts with enhanced reaction rate and reduced coking and byproduct formation, as compared to the conventional phosphoric acid-alumina catalysts. The catalysts include aluminotitanate and aluminosilicate prepared by either coprecipitation or impregnation. Japanese Patent 2-85224 to Mitsui Toatsu Chem Inc. (MITK) (1990) describes the use of γ-alumina doped with at least one oxide of Group IIIA metals for dehydration of methanol to DME. One or more salt(s) of Group IIIA metals were doped on high purity γ-alumina to 0.005 to 80 wt %, followed by calcination at 400° to 700° C. The catalyst is claimed to have long life time.

As documented below, aluminum phosphate based catalysts, either in bulk or supported form, are taught as catalyst supports and catalysts for a variety of reactions such as dehydration, isomerization, alkylation, hydrotreating, and cracking reactions. Aluminum phosphate based catalysts are not taught, however, for dehydrating methanol to DME within the single step DME process. This is not surprising because more readily available materials such as alumina, silica alumina, zeolite, and acidic resins are more active for simple dehydration of methanol to DME than aluminum phosphate due to their stronger acidity.

U.S. Pat. No. 3,342,750 (1967) to Esso Research and Engineering Company teaches an invention relating to high surface area aluminum phosphate gels, methods of making them, and methods of using them as catalysts or catalyst supports. The catalyst was made from an aqueous solution of aluminum chloride and phosphoric acid with ethylene oxide or ammonium hydroxide as the gelling reagent. The preparation is featured by careful control over pH, temperature and other conditions so that a hydrogel can be formed during precipitation. Washing procedure and medium also play an important role in the surface area of final materials. The gel loses its surface area readily on contact with water. The catalyst is claimed to be good for dehydration of alcohols to olefins or ethers, or for the reverse hydration reactions; but the only examples given are for oil cracking.

U.S. Pat. No. 3,904,550 (1975) to Exxon teaches a catalyst support material comprised of mixed alumina-aluminum phosphate. The content of aluminum phosphate ranges from 35 to 85 wt %. The material was prepared by reaction in aqueous medium of aluminum alkoxide with an inorganic or organic phosphorous-containing acid or soluble salt. The material was demonstrated as a catalyst support for the preparation of a platinum reforming catalyst.

U.S. Pat. No. 4,066,572 (1978) to Nalco Chemical Company teaches a catalyst or catalyst support composition consisting essentially of aluminum phosphate and the process of preparation. The material was precipitated from an aqueous solution containing at least one water soluble inorganic aluminum salt ($Al_2(SO_4)_3$) and at least one water soluble inorganic salt of an acid of phosphorous (($NH_4$) $H_2PO_4$) using an alkaline aqueous solution of a water soluble inorganic aluminate ($Na_2O \cdot Al_2O_3$+NaOH), followed by filtration, drying, purification, and calcination. The finished material is claimed to have large pore diameter (greater than 100 Angstroms) and minimal small pores. It is mentioned that the material can be used, in conjunction with Group VI and Group VIII transition metals or zeolites, in petroleum refining operations. An example was given of using this material as a catalyst support to prepare a desulfurization catalyst.

U.S. Pat. No. 4,080,311 (1978) to Gulf Research & Development describes thermally stable composite precipitates containing aluminum phosphate (40 to 90 mol %) and alumina (10 to 60 mol %) and their method of preparation. The invention is aimed at providing a more economic way to prepare mixed alumina-aluminum phosphate than the methods taught in U.S. Pat. Nos. 3,342,750 and 3,904,550. These materials were prepared by co-feeding an aqueous solution of aluminum cations (from aluminum nitrate, chloride, or sulfate) and $PO_4$ anions (from phosphoric acid) and a neutralizing medium, either ammonia gas or ammonia based materials such as ammonium hydroxide, ammonium carbonate, ammonium bicarbonate, and urea, to a common vessel, followed by filtration, washing, drying, and calcination. The scheme of neutralization is designed to provide a constant pH environment (7 to 10) for precipitation, which is claimed to be necessary for good thermal stability of the final products. The final materials have surface area ranging from 100 to 200 $m^2/g$ and pore radius from 75 to 150 Angstroms.

Another preparation for alumina-aluminum phosphate is described in U.S. Pat. No. 4,233,184 (1980) to Exxon. The precipitates were formed by reaction of a mixture of aluminum alkoxide and an organic phosphate (e.g., trialkyl or triaryl phosphate) in the presence of moist air, followed by drying and calcination. The aluminum phosphate in the final product may range from about 10 to about 90% by weight. The precipitates from this invention possess high surface area (400–600 $m^2/g$), and are much less sensitive on contact with water than the materials reported in U.S. Pat. Nos. 3,342,750 and 3,904,550. The material was tested for hydrotreating reactions.

U.S. Pat. No. 4,845,069 to the Dow Chemical Company (1989) claims a process for preparing amorphous, porous metallo phosphates. The metals include aluminum, titanium, barium, zirconium, hafnium, tantalum, chromium, molybdenum, wolfram, magnesium, scandium, copper, iron and lanthanum or their mixtures. The phosphates have average pore size from about 5 to about 50 Angstroms. The materials are claimed to be useful as catalysts and catalyst supports.

U.S. Pat. Nos. 5,030,431 (1991), 5,292,701 (1994), Re. 34,911 (1995), and European Patent 215 336 (1992) to W. R. Grace & Co. teach aluminum phosphate compositions and the method of making them. The material was prepared by neutralizing an acidic aqueous solution containing aluminum and phosphorus salts to form a gel, followed by soaking and washing with a basic solution, exchanging with an organic oxygenate, and drying. The finished material is characterized by high porosity and phosphorous-to-aluminum ratios of approximately 1.0. The compositions can be used as cracking catalysts, supports for ethylene polymerization catalysts, adsorbents, etc.. The composition comprising chromium was tested to the polymerization of ethylene.

Aluminum phosphate based materials have also been prepared through non-precipitation routes. As described in "Catalyst Manufacture—Laboratory and Commercial Preparation", A. B. Stiles (ed.), Marcel Dekker, Inc., New York, 1983, an aluminum phosphate catalyst is prepared by impregnating γ-alumina with 58% phosphoric acid, followed by drying and calcination at 300°–400° C. The loading of $P_2O_5$ on the alumina ranges from 10 to 20%. This material is used as dehydration catalyst.

Mixed alumina-aluminum phosphate can also be prepared by incorporating phosphorous oxide ($PO_4$) ions into alumina or its precursor. U.S. Pat. No. 3,969,273 (1976) to W. R. Grace & Co. describes a process for preparing phosphate-containing extruded alumina catalyst supports. The material was prepared by impregnating a dried gel-type alumina powder with a water soluble phosphate-containing compound, i.e., phosphoric acid or ammonium phosphate, followed by extruding, drying, and calcination. The phosphate content ranges from 1 to 10%.

U.S. Pat. No. 3,879,310 (1975) to Kaiser Aluminum & Chemical Corporation claims a surface stabilized active alumina and the process for making the material. The material was prepared by incorporating in a pseudoboehmitic alumina from about 1% to about 20% by weight $PO_4$ ions. Incorporation can be accomplished during the preparation of the pseudobohemitic alumina or by addition to freshly prepared pseudobohemitic alumina.

BRIEF SUMMARY OF THE INVENTION

The present invention pertains to a process for the coproduction of methanol and dimethyl ether (DME) directly from a synthesis gas in a single step (hereafter, the "single step DME process"). In this process, the synthesis gas comprising hydrogen and carbon oxides is contacted with a dual catalyst system comprising a physical mixture of a methanol synthesis catalyst and a methanol dehydration catalyst. The present invention is an improvement to this process for providing an active and stable catalyst system. The improvement comprises the use of an aluminum phosphate based catalyst as the methanol dehydration catalyst. Due to its moderate acidity, such a catalyst avoids the coke formation and catalyst interaction problems associated with the conventional dual catalyst systems taught for the single step DME process.

DETAILED DESCRIPTION OF THE INVENTION

Figure 1:
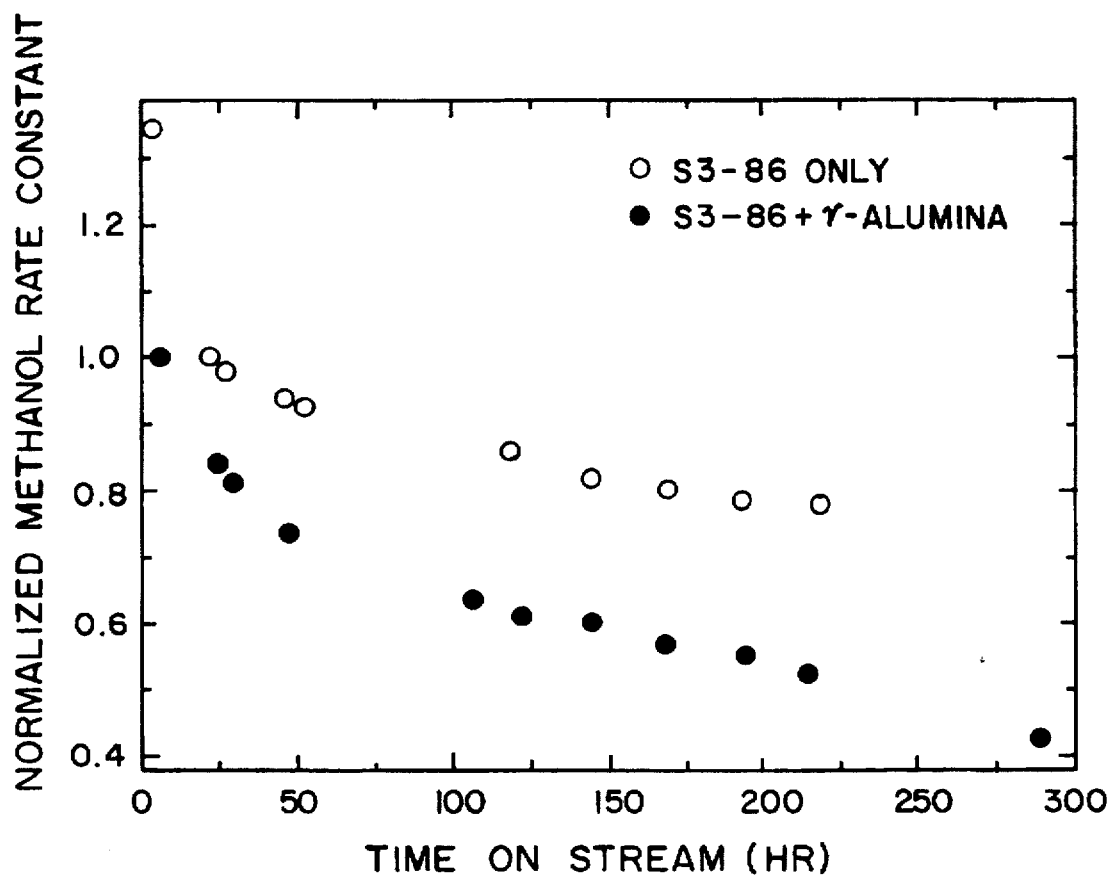
FIG. 1 is a graph in connection with Example 33 herein which illustrates the catalyst interaction problems of a conventional dual catalyst system taught for the single step DME process.

The present invention is a process for the coproduction of methanol and dimethyl ether (DME) directly from a synthesis gas in a single step which comprises contacting the synthesis gas comprising hydrogen and carbon oxides with a catalyst system comprising a physical mixture of (i) a methanol synthesis catalyst based on one or more compounds selected from the group consisting of copper, zinc, aluminum and chromium and (ii) a methanol dehydration catalyst based on aluminum phosphate.

The aluminum phosphate-based methanol dehydration catalyst used in the present invention is typically amorphous (although the crystalline form is also within the scope of the present invention) and is typically prepared by coprecipitating a water soluble aluminum salt and phosphoric acid using ammonium hydroxide as the precipitating reagent, followed by filtration, washing, drying, and calcination. The precipitation can also be carried out by precipitating a water soluble aluminum salt with a water soluble inorganic salt of an acid of phosphorous. The molar ratio of aluminum to phosphorus in the catalyst is in the range from about 0.4 to about 20.0, more preferably from about 1.0 to about 3.0. (It should be noted that, especially for high ratios of aluminum to phosphorous, the literature sometimes refers to aluminum phosphate as mixed alumina -aluminum phosphate). Additional purification and/or post treatments are used to achieve the desired purity and acid structure on the catalyst. The filter cake from the precipitation is washed using a solvent, e.g., water and isopropanol, one to three times, preferably three times. The post calcination temperature ranges from about 300° C. to 900° C., more preferably from about 600° C. to 850° C.

The process of the present invention can be operated in a liquid phase/slurry mode with a powder mixture of the two catalysts having a particle size of less than 200 microns. The concentration of catalyst in the liquid medium (typically a hydrocarbon based oil) is in the range from about 5 wt % to about 60 wt %. The process can also be carried out in a fixed bed reactor using pellets made of the powders of the two catalysts, or separate pellets of the two catalysts, or in a fluidized bed reactor using small beads made of the powders of the two catalysts, or separate beads of the two catalysts.

The preferred operating conditions of the process are a pressure range from about 200 psig to 2000 psig, more preferably from about 400 psig to about 1500 psig; a temperature range from about 200° C. to about 350° C.; and a space velocity in excess of 50 standard liters of synthesis gas per kilogram of catalyst per hour, more preferably in the range from about 1,000 to about 15,000 standard liters of synthesis gas per kilogram of catalyst per hour.

In the process of the present invention, synthesis gas is typically comprised of hydrogen, carbon monoxide, carbon dioxide, and often inert species such as nitrogen and $CH_4$. The composition of the gas can vary widely. When used in the slurry mode, the process is especially useful for higher carbon monoxide content synthesis gases, even where the concentration of carbon monoxide in the synthesis gas is in excess of about 50 vol %. Depending on feed concentration of hydrogen, carbon monoxide, and carbon dioxide, it may be advantageous to co-feed water either as a liquid or vapor to the process in order to adjust the gas composition via the water gas shift reaction. In addition it may be advantageous to remove carbon dioxide from the feed gas in order to affect the DME product selectivity. The removal of carbon dioxide can be accomplished by any conventional means, e.g., pressure swing adsorption or absorption using carbon dioxide selective solvents such as amines. The feed gas can be composed entirely of fresh feed in a once-through application, or it may be composed of a mixture of fresh feed and recycled gas.

Selectivity for DME and methanol in the present invention can be optimized by varying reaction conditions, synthesis gas compositions and/or the ratio of the two catalysts to suit specific end uses described hereinafter. Mixtures of DME and methanol can be used for their fuel value or for other applications based on specific chemical or physical properties. DME can be separated from the mixed product by known methods and recovered as a single product useful in a wide variety of applications, including as a diesel substitute, household fuel, and chemical building block.

Aluminum phosphate based catalysts are not taught for dehydrating methanol to DME within the single step DME process. As discussed previously, this is not surprising since more readily available materials such as alumina, silica alumina, zeolite, and acidic resins are more active for simple dehydration of methanol to DME than aluminum phosphate due to their stronger acidity. The key to the present invention is the recognition that, although acidity is good for dehydration activity, it is not very good for the stability of the dual catalyst system within the single step DME process. In particular, the use of aluminum phosphate in the present invention is based on a mechanistic understanding of the deactivation mechanism under syngas-to-DME reaction conditions: strong acid sites cause the deactivation of the methanol catalyst as well as the dehydration catalyst through coking and detrimental interaction. Due to the moderate acid strength of the aluminum phosphate catalyst, these problems are solved while still achieving acceptable dehydration activity.

In general, the prior art does not address the stability issue of the dual catalyst systems, although catalyst deactivation has been indicated in a number of them. Coking was recognized as a problem, and dealt with by passivating the strong acid sites on the dehydration catalyst, as shown in U.S. Pat. Nos. 4,536,458, 4,595,785, and 4,605,788, and Chinese Patent 1087033. Since the detrimental interaction between the two catalysts is due to a new and unique mechanism that was not known until recently, it was not a concern in the prior art. It is noted that most of the dehydration catalysts in the prior art are pure or modified alumina and zeolitic materials. The prior art neither teaches the use of materials with intrinsically weak or moderate acid strength to prevent coke formation, nor to prevent the detrimental interaction between methanol synthesis and dehydration catalysts. The present invention's use of an aluminum phosphate based catalyst as the methanol dehydration catalyst in the dual catalyst system avoids these problems associated with coke formation and catalyst interaction due to its moderate acidity (K. Tanabe, "Solid Acids and Bases", Academic Press, New York, 1970).

The following examples are offered to demonstrate the efficacy of the present invention.

EXAMPLE 1

A sample of aluminum phosphate catalyst was prepared by dissolving 150 gms of $Al(NO_3)_3 \cdot 9H_2O$ in 1125 ml dl $H_2O$ then adding 46.13 gms of 85% $H_3PO_4$ and stirring the mixture well. Separately, 141.75 gms of $NH_4OH$ (28–30%) was added to 300 ml dl $H_2O$. The $NH_4OH$ solution was added over a period 15 minutes to the aluminum phosphate solution to a final pH of 9.3. The precipitate obtained was filtered then the recovered solid was redispersed in 300 ml of isopropanol and filtered dry. The solid was further dried at 110° C. in an oven. The analyzed sample had an Al/P atomic ratio of 1.09.

EXAMPLE 2

A sample of aluminum phosphate catalyst was prepared by dissolving 150 gms of $Al(NO_3)_3 \cdot 9H_2O$ in 1125 ml dl $H_2O$ then adding 46.13 gms of 85% $H_3PO_4$ and stirring the mixture well. Separately, 141.75 gms of $NH_4OH$ (28–30%) was added to 300 ml dl $H_2O$. The $NH_4OH$ solution was added over a period 15 minutes to the aluminum phosphate solution to a final pH of 9.0. The precipitate obtained was filtered then the recovered solid was redispersed in 300 ml of deionized $H_2O$ and filtered dry. The solid was further dried at 110° C. in an oven. The analyzed sample had an Al/P atomic ratio of 1.22.

EXAMPLE 3

A sample of aluminum phosphate catalyst was prepared by dissolving 120 gms of $Al(NO_3)_3 \cdot 9H_2O$ in 750 ml dl $H_2O$ then adding 30.75 gms of 85% $H_3PO_4$ and stirring the mixture well. Separately, 141.75 gms of $NH_4OH$ (28–30%) was added to 300 ml dl $H_2O$. The $NH_4OH$ solution was added over a period 15 minutes to the aluminum phosphate solution to a final pH of 9.0. The precipitate obtained was filtered then the recovered solid was redispersed in 300 ml of isopropanol and filtered dry. The solid was further dried at 110° C. in an oven. The analyzed sample had an Al/P atomic ratio of 1.22.

EXAMPLE 4

A sample of aluminum phosphate catalyst was prepared by dissolving 160 gms of $Al(NO_3)_3 \cdot 9H_2O$ in 750 ml dl $H_2O$ then adding 30.75 gms of 85% $H_3PO_4$ and stirring the mixture well. Separately, 141.75 gms of $NH_4OH$ (28–30%) was added to 300 ml dl $H_2O$. The $NH_4OH$ solution was added over a period 15 minutes to the aluminum phosphate solution to a final pH of 9.2. The precipitate obtained was filtered then the recovered solid was redispersed in 300 ml of deionized $H_2O$ and filtered dry. The solid was further dried at 110° C. in an oven. The analyzed sample had an Al/P atomic ratio of 1.64.

EXAMPLE 5

A 15 gram specimen of aluminum phosphate catalyst prepared in Example 4 and dried only at 110° C. was retained. The dried only solid was redispersed and filtered an additional two times, each in 300 ml of deionized $H_2O$. The recovered solid was further dried at 110° C. in an oven.

EXAMPLE 6

A sample of aluminum phosphate catalyst was prepared by dissolving 150 gms of $Al(NO_3)_3 \cdot 9H_2O$ in 1125 ml dl $H_2O$ then adding 46.13 gms of 85% $H_3PO_4$ and stirring the mixture well. Separately, 141.75 gms of $NH_4OH$ (28–30%) was added to 300 ml dl $H_2O$. The $NH_4OH$ solution was added over a period of 180 minutes to the aluminum phosphate solution to a final pH of 9.0. The precipitate obtained was filtered then the recovered solid was redispersed in 300 ml of deionized $H_2O$ and filtered dry. The solid was further dried at 110° C. in an oven. The analyzed sample had an Al/P atomic ratio of 1.13.

EXAMPLE 7

A sample of aluminum phosphate catalyst was prepared by dissolving 160 gms of $Al(NO_3)_3 \cdot 9H_2O$ in 750 ml dl $H_2O$ then adding 30.75 gms of 85% $H_3PO_4$ and stirring the mixture well. Separately, 141.75 gms of $NH_4OH$ (28–30%) was added to 300 ml dl $H_2O$. The aluminum phosphate solution was added over a period 15 minutes to the $NH_4OH$ solution to a final pH of 9.2. The precipitate obtained was filtered then the recovered solid was redispersed in 300 ml of deionized $H_2O$ and filtered dry. The solid was further dried at 110° C. in an oven. The analyzed sample had an Al/P atomic ratio of 1.64.

EXAMPLE 8

A sample of aluminum phosphate catalyst was prepared by dissolving 220 gms of $Al(NO_3)_3 \cdot 9H_2O$ in 750 ml dl $H_2O$ then adding 30.75 gms of 85% $H_3PO_4$ and stirring the mixture well. Separately, 141.75 gms of $NH_4OH$ (28–30%)

was added to 300 ml dl H$_2$O. The NH$_4$OH solution was added over a period 15 minutes to the aluminum phosphate solution to a final pH of 8.9. The precipitate obtained was filtered then the recovered solid was redispersed in 300 ml of deionized H$_2$O and filtered dry. The solid was further dried at 110° C. in an oven. The analyzed sample had an Al/P atomic ratio of 2.12.

EXAMPLE 9

A sample of aluminum phosphate catalyst was prepared by dissolving 300 gms of Al(NO$_3$)$_3$·9H$_2$O in 750 ml dl H$_2$O then adding 30.75 gms of 85% H$_3$PO$_4$ and stirring the mixture well. Separately, 141.75 gms of NH$_4$OH (28–30%) was added to 300 ml dl H$_2$O. The NH$_4$OH solution was added over a period 15 minutes to the aluminum phosphate solution to a final pH of 9.0. The precipitate obtained was filtered then the recovered solid was redispersed in 300 ml of deionized H$_2$O and filtered dry. The solid was further dried at 110° C. in an oven. The analyzed sample had an Al/P atomic ratio of 3.07.

EXAMPLE 10

A large sample of aluminum phosphate catalyst was prepared by dissolving 615.2 gms of Al(NO$_3$)$_3$·9H$_2$O in 1533 ml dl H$_2$O then adding 118.2 gms of 85% H$_3$PO$_4$ and stirring the mixture well. Separately, 550.4 gms of NH$_4$OH (28–30%) without dilution was added over a period of 90 minutes to the aluminum phosphate solution to a final pH of 9.0. The precipitate obtained was filtered and 300 grams of the solid was removed for further experiments. The remaining recovered solid was redispersed in 2000 ml of deionized H$_2$O and filtered dry. This solid, dried at 110° C. in an oven, was analyzed and had an Al/P atomic ratio of 1.63.

The following two examples describe the preparation of two comparative samples.

EXAMPLE 11

Catapal B alumina was calcined in air at 500° C. 3.0 mL of (NH$_4$)$_2$HPO$_4$ solution (50% w/v) was added to 47 mL deionized H$_2$O. All of the phosphate solution was then added dropwise with frequent mixing to a 50 gram sample of the dry alumina to incipient wetness. The solid was dried at 110° C. in an oven. The analyzed sample contained 0.69 wt % P as the element. The dried only solid was then calcined by ramping in air at 10° C./minute to 650° C. and held for 2 hrs. This calcined sample contained 0.46% P as the element giving a final Al/P atomic ratio of 125.

EXAMPLE 12

Catapal B alumina was calcined in air at 500° C. 25.0 mL of (NH$_4$)$_2$HPO$_4$ solution (50% w/v) was added to 25 mL deionized H$_2$O. All of the phosphate solution was then added dropwise with frequent mixing to a 50 gram sample of the dry alumina to incipient wetness. The solid was dried at 110° C. in an oven. The analyzed sample contained 4.95 wt % P as the element. The dried only solid was then calcined by ramping in air at 10° C./minute to 650° C. and held for 2 hrs. This calcined sample contained 4.59% P as the element giving a final Al/P atomic ratio of 11.43.

Similarly, specimens of the catalysts from Examples 1 through 12 cited above were calcined at various temperatures for 2 hrs. These catalysts and their physical properties are given for Examples 13 through 27 in Table 1 below.

TABLE 1

| Example | Catalyst from Example # | Measured Al/P Ratio | Calcination Temp. (C.) | Surface Area (m²/g) | Pore Volume (cc/g) | Median Pore Diam. (A) |
| --- | --- | --- | --- | --- | --- | --- |
| 13 | 1 | 1.09 | 650 | 191 | 0.505 | 141 |
| 14 | 1 | 1.09 | 450 | n.a. | n.a. | n.a. |
| 15 | 2 | 1.22 | 650 | 160, 210 | 0.597 | 139 |
| 16 | 3 | 1.22 | 650 | 211, 227 | 0.962 | 282 |
| 17 | 4 | 1.64 | 650 | 190, 180 | 0.555 | 153 |
| 18 | 4 | 1.64 | 750 | 176 | n.a. | n.a. |
| 19 | 7 | 1.64 | 650 | 154 | n.a. | n.a. |
| 20 | 8 | 2.12 | 650 | 201, 234 | 0.812 | 192 |
| 21 | 8 | 2.12 | 750 | n.a. | n.a. | n.a. |
| 22 | 9 | 3.07 | 650 | 226, 232 | 0.733 | 169 |
| 23 | 9 | 3.07 | 750 | n.a. | n.a. | n.a. |
| 24 | 10 | 1.63 | 650 | 209, 207 | 0.458 | 91 |
| 25 | 10 | 1.64 | 750 | 204, 205 | 0.435 | 89 |
| 26 | 11 | 125 | 650 | 185 | n.a. | n.a. |
| 27 | 12 | 11.4 | 650 | 112 | n.a. | n.a. |

Additional specimens of catalysts from Examples 1 through 12 cited above were redispersed/washed in deionized H$_2$O a total of three (3) times, dried at 110° C., then similarly calcined at 650° C. for 2 hrs. These catalysts and their physical properties are pared in Examples 28 through 32 in Table 2 below with those which were redispersed only once.

TABLE 2

| Example | Catalyst from Example # | Washes | Calcination Temp. (C.) | Measured Al/P Ratio | Surface Area (m²/g) |
| --- | --- | --- | --- | --- | --- |
| 17 | 4 | 1 | 650 | 1.64 | 190, 180 |
| 28 | 5 | 3 | 650 | 1.64 | 159 |
| 29 | 6 | 1 | 650 | 1.18 | 158, 163 |
| 30 | 6 | 3 | 650 | 1.18 | 172 |
| 24 | 10 | 1 | 650 | 1.63 | 209, 207 |
| 31 | 10 | 3 | 650 | 1.68 | 218, 214 |

The performance of these materials was evaluated in a liquid phase process for the production of DME (LPDME) from synthesis gas. All runs were carried out in 300 cc stainless steel autoclave reactors under the same conditions and procedure. The feed and product gas were analyzed via gas chromatograph. In all of the runs (except run #1), 8 grams of BASF S3-86 methanol synthesis catalyst (approximately 40 wt % of CuO on a special support with an average particle size of less than 50 microns) was charged into the reactor along with 2 grams of the methanol dehydration catalyst and 120 grams of Drakeol 10 mineral oil. In Run #1, 10 grams of the methanol synthesis catalyst was charged into the reactor without any dehydration catalyst. The methanol catalyst in all runs was reduced in situ using 2% H$_2$ in N$_2$, and a standard temperature ramp (about 24 hours from ambient temperature to 240° C.), followed by the introduction of the syngas to the reactor. The syngas contained 30% H$_2$, 66% CO, 3% CO$_2$, and 1% of N$_2$. The reaction temperature, pressure and gas hourly space velocity (GHSV) were 250° C., 750 psig, and 6,000 mol/kg-hr, respectively. The duration of the runs ranged from 150 to 934 hours on syngas stream.

The following criteria were used to evaluate the performance of the catalysts: dehydration activity, dehydration catalyst stability, methanol synthesis catalyst stability, and methanol equivalent productivity. The dehydration activity is expressed in terms of the dehydration rate constant, $k_d$, calculated from the rate expression below:

$$R_d = k_d f^{-0.33}_{CO_2} f^{0.11}_{MEOH} f^{0.70}_{CO}(1-\text{appr.})[\text{mol/kg-cat./hr}]$$

where f stands for fugacity in unit of atm and appr. is the approach to reaction equilibrium.

The stability of the methanol catalyst is an important criterion because it is an indication of the negative effect of a dehydration catalyst on the methanol catalyst through the detrimental interaction. This stability is measured by the decreasing rate of the methanol synthesis rate constant, $k_m$, normalized by the initial value, with time on stream. The rate constant was calculated using the kinetic model below:

$$R_m = k_m f^{2/3}_{H_2} f^{1/3} c_O (1-\text{appr.})[\text{mol/kg-cat./hr}]$$

The methanol equivalent productivity was defined as the moles of methanol plus two times the moles of DME produced over per kilogram of catalyst per hour.

EXAMPLE 32

Aluminum phosphate catalysts from Examples 13 to 25 and 28 to 31 cited above were evaluated for their performance under the LPDME conditions described above. Results are presented in Table 3. Table 3 also includes the results from the comparative samples, including γ-alumina impregnated with phosphate from Examples 26 and 27, and pure γ-alumina derived from Catapal B alumina by calcination at 500° C. for 3 hours.

TABLE 3

| Run | Dehydration Catalyst Example # | Dehydration Activity ($k_d$) | Dehydration Catalyst Stability | MeOH Cat. Stability (%/hr) | Productivity Me + 2 DME (mol/kg-hr) |
|---|---|---|---|---|---|
| 1 | none | not appl. | not appl. | −0.042 | 15.0 |
| 2 | 13 | 5.7 | stable | −0.032 | 24.6 |
| 3 | 14 | 5.1 | stable | −0.110 | 23.8 |
| 4 | 15 | 6.8 | stable | −0.049 | 26.2 |
| 5 | 16 | 5.8 | stable | −0.120 | 24.6 |
| 6 | 17 | 8.0 | stable | −0.071 | 29.0 |
| 7 | 18 | 7.7 | stable | −0.040 | 29.1 |
| 8 | 19 | 5.7 | stable | −0.190 | 25.2 |
| 9 | 20 | 6.3 | small deact. | −0.062 | 26.0 |
| 10 | 21 | 4.8 | stable | −0.050 | 24.2 |
| 11 | 22 | 7.5 | stable | −0.038 | 28.0 |
| 12 | 23 | 6.4 | stable | −0.059 | 26.2 |
| 13 | 25 | 7.1 | stable | −0.082 | 27.3 |
| 14 | 28 | 6.4 | stable | −0.038 | 27.2 |
| 15 | 30 | 5.6 | stable | −0.067 | 26.0 |
| 16 | 31 | 6.4 | stable | −0.110 | 26.8 |
| 17 | 26 | 14.1 | rapid deact. | −0.28 | 33.5 |
| 18 | 27 | 5.6 | not stable | −0.150 | 26.2 |
| 19 | γ-alumina | 17 | rapid deact. | −0.26 | 31.0 |

EXAMPLE 33

This example compares the stability of BASF S3-86 methanol catalyst under gas phase reaction conditions when used by itself and when used along with γ-alumina. The γ-alumina was prepared by calcining Catapal B alumina at 500° C. for 3 hours. TWO runs were carried out in a packed bed reactor with a copper liner. In the methanol synthesis run using the methanol catalyst only, S3-86 powder less than 200 mesh was pressed into pellets of approximately 0.5 mm in diameter. For the DME run, a powder mixture containing 80 wt % of S3-86 and 20% of γ-alumina, both less than 200 mesh, was pressed into pellets of the same size. The same quantity of S3-86, 0.11 grams, was used in each run. The feed gas was composed of 35% $H_2$, 51% CO, 13% $CO_2$, and 1% of $N_2$. To minimize the exotherm in the packed bed and to make the gas phase composition close to each other in the two runs, the conversion was kept low (<2% CO) by operating at high GHSV (130,000 sl/kg-hr in each case). The two runs were carried out at 250° C. and 750 psig. FIG. 1 depicts the normalized methanol synthesis rate constant as a function of time on stream for the two runs. It shows that the rate of deactivation of the methanol catalyst is greater when used with γ-alumina. This indicates that the detrimental interaction between the two catalysts also takes place under gas phase reaction conditions.

Figure 2:
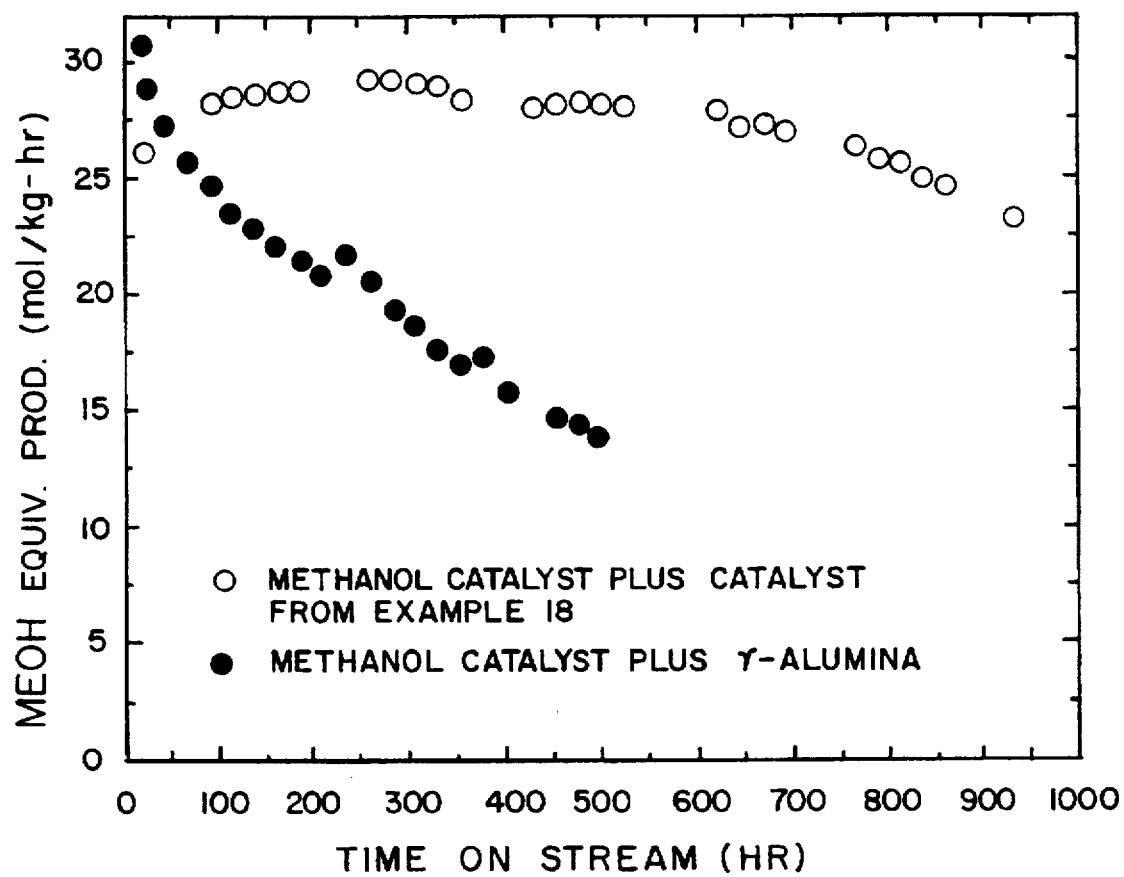
FIG. 2 is a graph which compares the methanol equivalent productivity of one embodiment of the present invention via-a-vis a conventional dual catalyst system.

The aluminum phosphate based methanol dehydration catalyst in the present invention, when used along with the methanol synthesis catalyst, exhibit decent productivity of DME and methanol from syngas. FIG. 2 depicts the methanol equivalent productivity as a function of time on stream for the dual catalyst system containing an aluminum phosphate catalyst (Run 7) and the dual catalyst system containing γ-alumina (Run 19), respectively. Although the dehydration activity of the aluminum phosphate catalyst is smaller than that of traditional dehydration catalysts such as γ-alumina, the initial methanol equivalent productivity from the two dual catalyst systems are comparable. This is due to the following two factors. First, the methanol catalyst in the alumina-containing catalyst system had suffered deactivation, owing to the detrimental interaction with γ-alumina, during the 24 hour reduction period prior to the introduction of the syngas. No such deactivation occurred in the aluminum phosphate-containing catalyst system, resulting in higher methanol synthesis activity. As shown in Table 3, all aluminum phosphate catalysts (Runs 2 through 16) have lower dehydration activity than γ-alumina, with an average $k_d$ of 6.4 versus 17 for γ-alumina (Run 19); but the productivity from these catalyst systems is within 77% of the initial productivity from the alumina-containing catalyst system. Secondly, although aluminum phosphate is a moderate acid, its dehydration activity is compensated by the fact that it forms a high surface area material. As shown in Tables 1 and 2, the surface area of the aluminum phosphate catalysts ranges from about 160 $m^2/g$ to about 240 $m^2/g$.

The primary advantage of the present invention is the excellent stability of the dual catalyst system. As shown in FIG. 2 and Table 3, the methanol catalyst is much more stable when used with the aluminum phosphate catalysts than with γ-alumina. The deactivation rate of the methanol catalyst, when used with the catalysts from Examples 13, 15, 18, 21, 22 and 28, was in a range from 0.032% $hr^{-1}$ to 0.050% $hr^{-1}$, similar to that when the methanol catalyst was used by itself (0.042% $hr^{-1}$, Run 1), considering the experimental noise. The deactivation rate for most of the other runs with aluminum phosphate catalysts never exceeded 0.12% $hr^{-1}$, a factor of 2.2 slower than with γ-alumina (0.26% $hr^{-1}$). (Example 19 is an exception with a rate of 0.19% $hr^{-1}$.) Moreover, the aluminum phosphate catalysts were stable themselves in all cases, while γ-alumina deactivated rapidly. Because of the better stability for both methanol synthesis and methanol dehydration catalysts, the methanol equivalent productivity of the dual catalyst system containing the aluminum phosphate catalysts all exceeds that of the catalyst system containing γ-alumina after 100 hours on stream.

Although aluminum phosphate based catalysts are known and used for dehydration of alcohols in the prior art, the negative effect on a co-existing methanol catalyst was never a concern in the preparation of these materials. That is, none of the preparations used special formulations or took deliberate preparation steps to minimize this effect. In this work, it was discovered that elimination of this negative effect requires aluminum phosphate of high purity and some specific acid structures, which is very sensitive to the preparation and post treatment. For instance, catalysts from Examples 13 and 14 were from the same preparation, but calcined at 650° C. and 450° C., respectively. As shown by Runs 2 and 3, the higher temperature calcination resulted in better methanol catalyst stability. The same trend was observed from the catalyst pairs from Examples 17 and 18, and, 20 and 21.

More thorough wash also exhibited effects on the stability of the methanol catalyst. Catalysts from Examples 17 and 28 were from the same preparation, except that the former was washed a single time with deionized water and the latter three times. Washing three times resulted in much better methanol catalyst stability, as shown by Runs 6 and 14.

Whether aluminum phosphate is in bulk or supported form also makes a difference. Runs 17 and 18 in Table 3 show that the supported form of aluminum phosphate did not perform well under liquid phase DME conditions. The catalyst from Example 26 with a low loading of phosphorus on γ-alumina (0.46 wt %) acted similarly to pure γ-alumina, i.e., rapid deactivation of both catalysts. The phosphorus loading on the catalyst from Examples 27 was higher, 4.59 wt %. Its negative effect on the methanol catalyst stability is less severe as compared to γ-alumina, but more as compared to all the bulk aluminum phosphate catalysts. Furthermore, the catalyst itself was not stable under the reaction conditions.

The skilled practitioner will further appreciate that there are many embodiments of the present invention which are within the scope of the following claims.

We claim:

1. In a process for the coproduction of methanol and dimethyl ether directly from a synthesis gas in a single step which comprises contacting the synthesis gas comprising hydrogen and carbon oxides with a dual catalyst system comprising a physical mixture of (i) a methanol synthesis catalyst based on one or more compounds selected from the group consisting of copper, zinc, aluminum and chromium and (ii) a methanol dehydration catalyst;

the improvement to the above process for increasing the stability of said dual catalyst system comprising using a catalyst comprising aluminum phosphate as said methanol dehydration catalyst.

2. The process of claim 1 wherein the molar ratio of aluminum to phosphorus in the methanol dehydration catalyst is in the range from about 1.0 to about 3.0.

3. The process of claim 1 wherein said catalyst comprising aluminum phosphate is prepared by coprecipitating a water soluble aluminum salt and phosphoric acid using ammonium hydroxide as a precipitating agent followed by filtration, washing, drying and calcination.

4. The process of claim 1 wherein the process is conducted in the liquid phase such that the synthesis gas is contacted with the catalyst system in powder form in a slurry phase reactor containing an inert liquid medium.

\* \* \* \* \*